United States Patent
Rein et al.

(10) Patent No.: US 9,833,298 B2
(45) Date of Patent: Dec. 5, 2017

(54) DENTISTS' PREPARATION INSTRUMENT

(71) Applicant: Sirona Dental Systems GmbH, Bensheim (DE)

(72) Inventors: Matthias Rein, Lorsch (DE); Siegfried Goisser, Einhausen (DE); Metin Ertugrul, Rodermark (DE); Ralf Sutter, Weinheim (DE)

(73) Assignee: Sirona Dental Systems GmbH, Bensheim (DE)

( * ) Notice: Subject to any disclaimer, the term of this patent is extended or adjusted under 35 U.S.C. 154(b) by 22 days.

(21) Appl. No.: 14/415,547

(22) PCT Filed: Jul. 17, 2013

(86) PCT No.: PCT/EP2013/065051
§ 371 (c)(1),
(2) Date: Jan. 16, 2015

(87) PCT Pub. No.: WO2014/012958
PCT Pub. Date: Jan. 23, 2014

(65) Prior Publication Data
US 2015/0173851 A1    Jun. 25, 2015

(30) Foreign Application Priority Data
Jul. 17, 2012 (DE) ......................... 10 2012 212 483

(51) Int. Cl.
*A61C 1/05*  (2006.01)
(52) U.S. Cl.
CPC ................... *A61C 1/05* (2013.01)

(58) Field of Classification Search
CPC ................. A61C 1/05; A61C 1/057
(Continued)

(56) References Cited

U.S. PATENT DOCUMENTS 3,952,416 A * 4/1976 Lingenhole ............ A61C 1/052
                                                        433/104
5,374,189 A * 12/1994 Mendoza ............. A61C 17/005
                                                        433/125
(Continued)

FOREIGN PATENT DOCUMENTS

DE    43 20 532 C1    9/1994
DE    44 28 039 C1    11/1995
(Continued)

OTHER PUBLICATIONS

Office Action issued in German Patent Application No. 10 2012 212 483.7, dated Feb. 19, 2013.
(Continued)

*Primary Examiner* — Nicholas Lucchesi
(74) *Attorney, Agent, or Firm* — Fitzpatrick, Cella, Harper & Scinto

(57) ABSTRACT

A dental apparatus that includes a turbine, a rotor, and a disruptive contour. The turbine drives a tool by compressed air. The rotor is arranged in a turbine compartment and rotates about its longitudinal axis. The rotor includes a plurality of blades that extend up to a front side of the rotor. The disruptive contour is at least one protrusion on a wall opposite the front side of the rotor which extends over a height in a direction of the longitudinal axis of the rotor.

22 Claims, 3 Drawing Sheets

(58) Field of Classification Search
USPC .................................................. 433/120, 132
See application file for complete search history.

(56) References Cited

U.S. PATENT DOCUMENTS

| | | | |
|---|---|---|---|
| 5,496,173 A | 3/1996 | Wohlgemuth | |
| 5,567,154 A * | 10/1996 | Wohlgemuth | A61C 1/05 415/904 |
| 6,676,374 B2 | 1/2004 | Hashimoto et al. | |
| 2001/0002975 A1* | 6/2001 | Hashimoto | A61C 1/05 415/202 |
| 2008/0070189 A1* | 3/2008 | Turner | A61C 1/05 433/132 |

FOREIGN PATENT DOCUMENTS

DE     100 60 152 A1    6/2001
EP      0 497 139 A1    8/1992

OTHER PUBLICATIONS

International Preliminary Report on Patentability in PCT Application No. PCT/EP2013/065051, dated Jan. 20, 2015.

\* cited by examiner

DENTISTS' PREPARATION INSTRUMENT

CROSS-REFERENCE TO RELATED APPLICATIONS

This application is a national stage entry of PCT/EP2013/065051 filed Jul. 17, 2013, which claims priority to German Patent Appln. No. 10 2012 212 483.7 filed Jul. 17, 2012.

BACKGROUND OF THE INVENTION

Field of the Invention

The invention relates to a dentists' preparation instrument having a turbine for driving a tool by means of compressed air. A rotor arranged in a turbine compartment and rotating about a longitudinal axis has blades extending to a face of the rotor. The turbine compartment has a wall opposite the face and has a discharge port for the compressed air to a return air duct, wherein the discharge port is arranged in the turbine compartment in such a way that at least parts of the blades of the rotor pass by the discharge port in rotation about the longitudinal axis.

Description of the Related Art

In known dentists' preparation instruments having a turbine drive, also known as dental turbines, compressed air is used to drive a rotor. The kinetic energy of the air causes an impulse on the blades of the rotor through an exchange of momentum. From this impulse, a torque is created on the rotor, and the resulting rotational speed depends primarily on the speed of the air flowing out of the nozzle during idling. At the idling speed, i.e., during no-load operation of the turbine, the torque and thus the usable power approach zero while the maximum power is established at half the idling speed in a characteristic manner. However, increasing the idling speed to increase the maximum power has a negative effect on the lifetime of the bearings and on the noise level of turbines.

DE 100 60 152 B4 describes a dental turbine hand piece in which a rotor is equipped with a first and a second turbine wheel to increase the torque, and connecting ducts are provided to deflect the pressurized medium from the first turbine wheel to the second turbine wheel. In one embodiment, the flow passes twice through the second turbine wheel, which brakes the rotor and reduces the rotational speed.

The object of the invention is to achieve a reduction in the idling speed in order to improve the lifetime and noise behavior without restricting the maximum torque or the effective power to an extent that would be of practical relevance.

BRIEF SUMMARY OF THE INVENTION

The dentists' preparation instrument having a turbine for driving a tool by means of compressed air according to the invention comprises a rotor arranged in a turbine compartment and rotating about a longitudinal axis, having blades that extend to a front side of the rotor. The turbine compartment has a wall opposite the front side and a discharge port for the compressed air toward a return air duct, wherein the discharge port is arranged in the turbine compartment in such a way that at least parts of the blades of the rotor pass by the discharge port in rotation about the longitudinal axis. The turbine compartment has a disruptive contour chamber adjacent to the front side, wherein the front side of the blades of the rotor, the front side being turned toward the disruptive contour chamber, is open toward the disruptive contour chamber, and a disruptive contour formed by at least one protrusion extending in the direction of the longitudinal axis on the wall opposite the front side is arranged in the disruptive contour chamber.

This disruptive contour in the disruptive contour chamber of the turbine compartment alters the direction of the air flow in the disruptive contour chamber from a direction of flow with the rotor in the circumferential direction to a direction of flow along the longitudinal axis to the rotor by means of the oncoming flow against the disruptive contour and creates a braking force, which depends greatly on the rotational speed. The peripheral velocity of the air in the disruptive contour chamber is lower in the region of the disruptive contour than the circumferential velocity of the rotor, and a stagnation pressure develops and thus a torque also develops opposite the direction of rotation of the rotor, so the rotational speed decreases. Since the braking power depends on the rotational speed in the third order, the braking power at low rotational speeds is much lower than at high rotational speeds, so the braking power can be adapted to the particular turbine by means of the geometry of the disruptive contour.

This idling brake does not have any wearing parts and can be manufactured easily, reliably and inexpensively. In addition, it is not necessary to alter the rotors or the blade geometry of known turbines.

The disruptive contour arranged in the disruptive contour chamber may advantageously be at a distance of at least 0°, preferably of 10° to 50°, especially preferably of 30° from the discharge port in an angular range in the circumferential direction, as seen in the direction opposite the direction of rotation of the rotor.

If the disruptive contour is mounted directly in the outlet, a portion of the air provided for braking can escape directly through the discharge port so that the braking power and thus the braking effect are reduced. A distance from the discharge port, such as that beyond an angle of 0° and most especially an angle of 30°, increases the braking effect and achieves the result that the oncoming flow of the disruptive contour in the disruptive contour chamber is largely free from the influence of an outlet eddy and manifests its effect largely independent of the latter, so the effect can be scheduled.

A distance from the discharge port with an angle of 30° to the discharge port is therefore particularly suitable because the disruptive contour is also far enough away from a nozzle for driving the rotor. First, boundary effects caused by a nozzle for the compressed air for driving the rotor will have then subsided; second, the effect of the nozzle is not influenced by the brake. A great distance from the nozzle thus means low power losses. It has thus been found that the distance from the discharge port with an angle of 30° is a compromise in which the power is maximal and the idling speed is minimal at the rated speed.

The disruptive contour arranged in the disruptive contour chamber advantageously has a height of at least 0.25 mm in the direction of the longitudinal axis and may have a width of the gap between the disruptive contour and the front side of the rotor of up to 1 mm, preferably 0.1 mm. It has been found that with these dimensions, a good compromise is achieved between the desired braking power in idling and the manufacturing tolerances.

The disruptive contour may advantageously have a width b, as viewed in the circumferential direction, which covers at most two blades at the same time on the outside circumference of the blades and amounts to at least 0.1 mm, wherein it has been found that good results are achieved when the width b corresponds to the height h of the protrusion 14. A value of 0.9 mm has been found to be particularly suitable for the width b and for the height h.

The highest velocities of flow are achieved on the outside circumference, and deflection of the air flow into another direction of flow leads to the greatest differences in velocity, so that the braking effect is greatest. Since the rotor is mounted on the shaft, the disruptive contour can extend no farther than up to this shaft.

The disruptive contour chamber may advantageously be arranged above the rotor. To be sure, a disruptive contour above, which is usually shaped into a cover module with an additional component and a cover, requires precise coordination of two components, namely the additional component of the cover module, on the one hand, and the head housing, on the other hand, for accurate positioning of the disruptive contour in relation to the discharge duct, but retrofitting of existing turbines with a brake is readily possible by replacing the old cover, and existing turbines can be upgraded in this way.

Another advantage is that the force acting on the brake also acts on the cover or on the additional component and tightens it. An independent release is no longer possible in this way, even for a cover module that has been tightened only by hand, wherein it is assumed that this involves a right-hand thread and turbines rotating clockwise.

The disruptive contour chamber may advantageously be arranged below the rotor toward the tool side. If the disruptive contour is mounted on the tool side in the head part, then the position is defined precisely in relation to the discharge duct in the process of manufacturing the head housing, which is a materials-removal process. The angular position of the disruptive contour is formed in a machining step within a single component, so that the disruptive contour can be manufactured easily in terms of the manufacturing technology and with a high precision. Furthermore, this arrangement permits better utilization of the available space in the head housing and also prevents the head part from protruding outward in relation to the neck of the turbine.

To achieve a maximum braking effect, the two arrangements can be implemented at the same time, wherein it is then necessary to ensure that both front surfaces of the rotor and/or the blades are open.

However, the disruptive contour chamber may be additionally limited in the radial direction with respect to the shaft, for example, due to a formation on the housing or a disk with a collar protruding toward the rotor and cooperating with a hub on the rotor. The disruptive contour chamber is sealed in this way and the flow can be guided efficiently.

The disruptive contour may advantageously be arranged on the outside circumference of the wall of the braking chamber and may extend partially or completely radially up to the collar.

A braking contour, which cooperates with the disruptive contour, may advantageously be provided on the front side of the blades of the rotor facing the disruptive contour chamber. This has the advantage that the braking performance can be further increased because this braking contour on the rotor may be designed for this altered air flow in particular. The braking contour may in particular have a height in the direction of the longitudinal axis of at least 5% of the height of the blades, preferably more than 15% and at most 75%.

The disruptive contour chamber may advantageously be bordered by a cover module, consisting of at least one cover and an intermediate part supporting the cover and connected to the housing.

BRIEF DESCRIPTION OF THE DRAWINGS

The invention will now be explained on the basis of the drawings, which show.

DETAILED DESCRIPTION OF THE INVENTION

Figure 1:
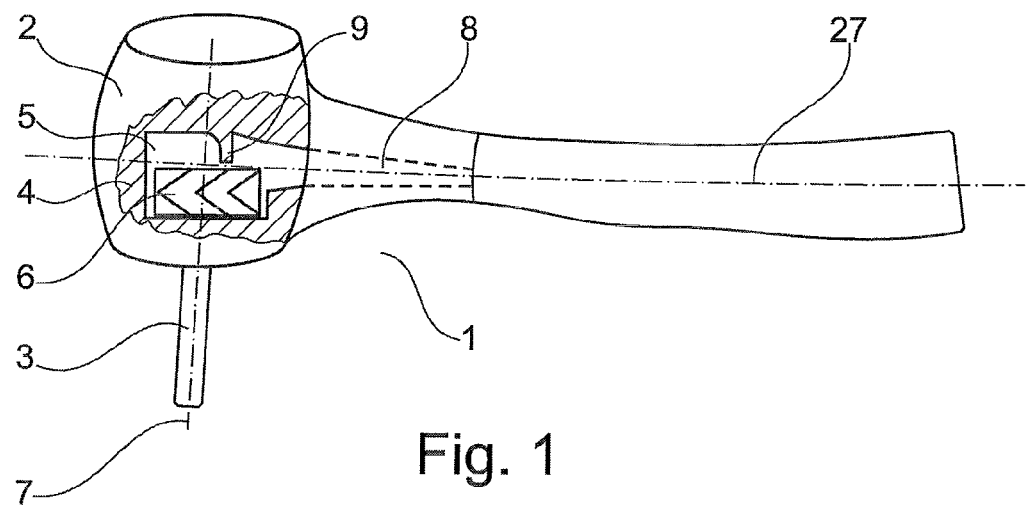
FIG. 1 a side view of a dentists' preparation instrument having an idling brake according to the invention for a turbine.

FIG. 1 shows schematically a dentists' preparation instrument 1 in a partially cut-away side view, wherein the said instrument has a turbine 4, which is acted upon with compressed air to drive a tool 3, which is supported in a head part 2 and driven. The turbine 4 comprises a turbine compartment 5, in which a rotor 6 is mounted so it can rotate about a longitudinal axis 7. The bearing of the rotor 6 in the head part 2 itself and the cooperation of the rotor 6 with the tool 3 are not shown here, but reference is made in this regard to the prior art from which a wide variety of different approaches are known, for example, in the documents cited in the introduction. The preparation instrument 1 has a central axis 27, which also passes through the head part 2.

In addition to a compressed air feed (not shown), a return air duct 8, which guides the compressed air out of the turbine compartment 5, is provided in the head part 2, so that the compressed air is guided through a handle part to a coupling part of the preparation instrument, as is also known from the prior art.

Figure 2:
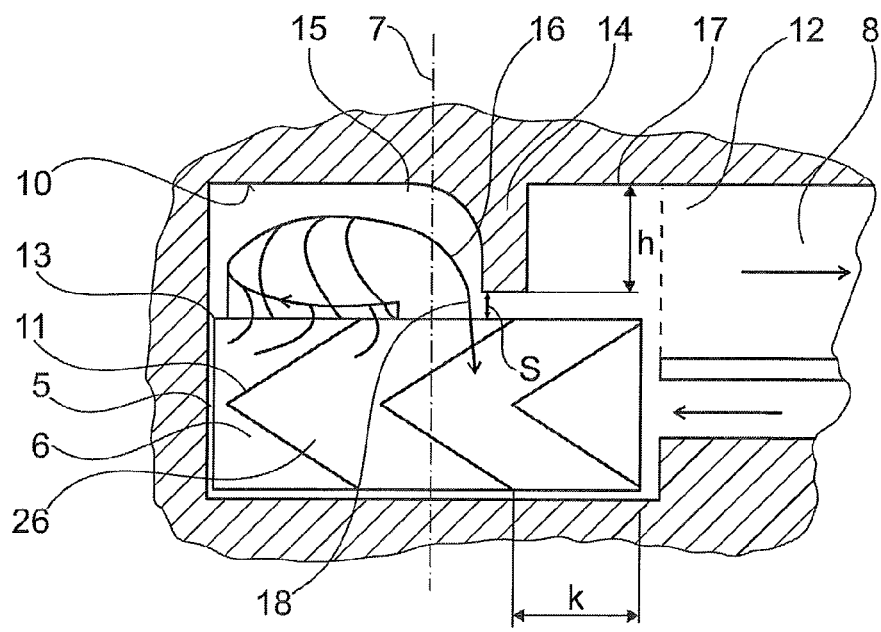
FIG. 2 the turbine from FIG. 1 in a detail view in a longitudinal section with a turbine compartment having a disruptive contour chamber and a disruptive contour arranged therein.
Figure 3:
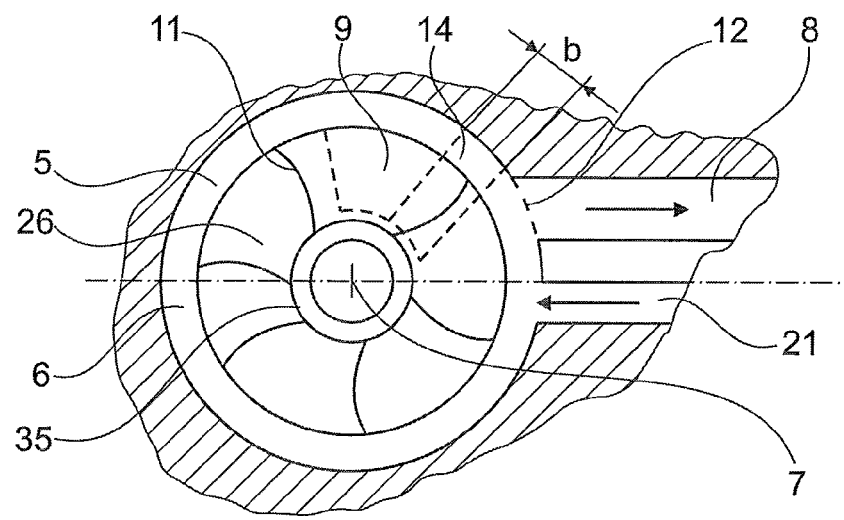
FIG. 3 the turbine from FIG. 2 in a cross section through the turbine compartment.

It can already be seen in FIG. 1 that the turbine compartment is provided with a disruptive contour 9, which is arranged in the turbine compartment 5 together with the rotor 6. FIGS. 2 and 3 illustrate the functioning of this disruptive contour 9 and the interaction with the other functional components.

FIG. 2 illustrates the turbine compartment 5 with the rotor 6 in detail, wherein this is still a schematic diagram in which the bearing of the rotor 6, for example, has been omitted for reasons of simplicity. The disruptive contour 9 is arranged on a wall 10 of the turbine compartment 5. The rotor 6 has blades 11, which deflect the compressed air provided for the drive of the turbines to improve efficiency. The compressed air flowing away from the blades 11, also referred to as exhaust air, leaves the turbine compartment 5 through a discharge port 12, which connects the turbine compartment 5 to the return air duct 8 and thus enters the return air duct 8.

The discharge port 12 is arranged in the turbine compartment 5 in such a way that, when rotating about the longitudinal axis 7, a front side 13 of the rotor 6 passes by the discharge port 12 as well as parts of the blades 11.

The front side 13 of the rotor is opened with respect to the blades 11, so that air can also flow out of the blades and over the front side 13.

The disruptive contour 9 present on the wall 10 opposite the front side 13 is formed by a protrusion 14, so that a disruptive contour chamber 15, in which the disruptive contour 9 is accommodated, is formed within the turbine compartment 5, viewed with respect to the function. The discharge port 12 partially also extends in height over the disruptive contour chamber 15 along the longitudinal axis 7. As a result, the discharge port 12 has an outlet cross section, which is of dimensions such that some of the blades 11 as well as at least some of the air having passed by the disruptive contour 9 flows past the discharge port 12.

Figure 4:
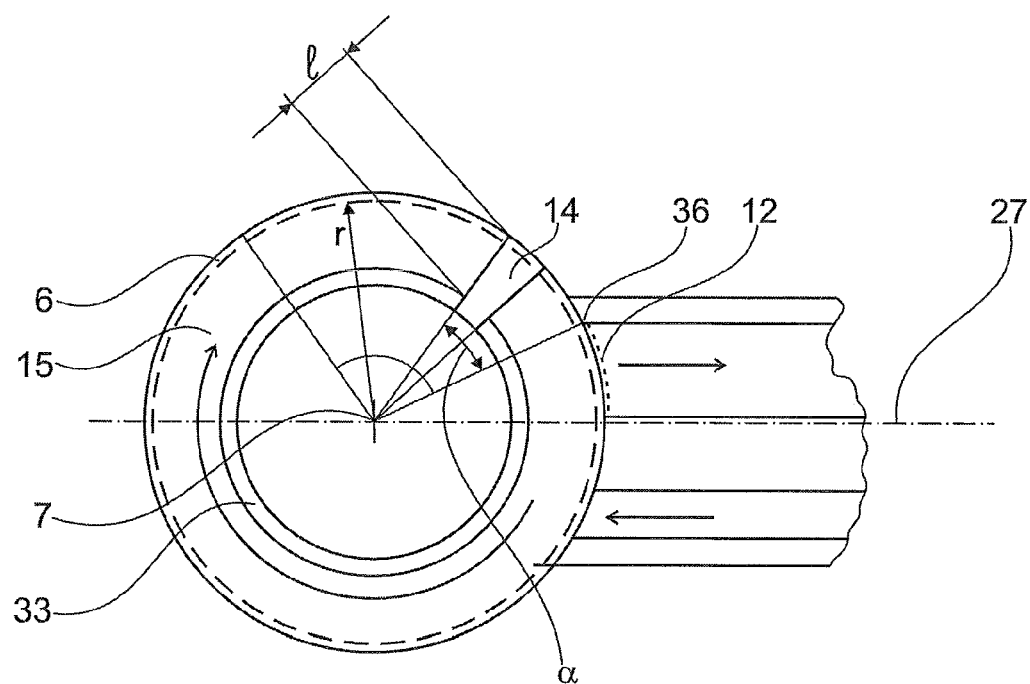
FIG. 4 the turbine compartment without the rotor in a view of the front wall with the disruptive contour.

The protrusion 14 on the disruptive contour 9 may also be formed by one or more ribs or webs protruding beyond the wall 10, as shown in the view of the brake contour in FIG. 3 and in particular FIG. 4. The protrusion 14 is arranged on the outside circumference in the disruptive contour chamber 15.

Because of the protrusion 14 in the disruptive contour chamber 15, the air flow circulating with the rotor 6 above the face of the rotor 6 is deflected, as represented schematically by the arrow 16. The air flow experiences a constriction of cross section at the protrusion 14 due to the disruptive contour. The portion of the exhaust air which is in the disruptive contour chamber 15 is forced into a blade space 26, which is situated between the blades 11 in passing by the disruptive contour 9, with a blade spacing k, which provides an empty blade volume. This results in a delay of these air particles and thus a pressure acting on the rotor blades in the direction opposite the direction of rotation. This effect is greatly pronounced in the region of the disruptive contour and declines upstream. The effect has largely subsided after passing by the disruptive contour.

Figure 5:
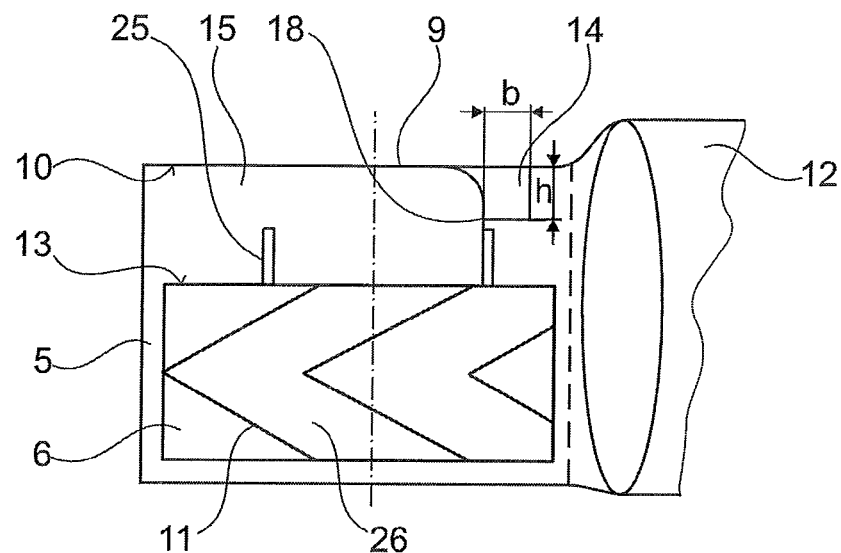
FIG. 5 a rotor having a braking contour in a turbine compartment according to the invention.

The disruptive contour 9 has a width b, which is shown in FIG. 3 and FIG. 5, as seen in the circumferential direction, simultaneously covering at most two blades 11 and amounting to at least 0.1 mm, measured on the outside circumference, wherein it has been found that good results are achieved if the width b corresponds to the height h of the protrusion 14. A value of 0.9 mm has been found to be particularly suitable for the width b and the height h.

The shape of the disruptive contour 9 may be optimized in terms of fluid mechanics.

FIG. 3 shows the turbine from FIG. 2 in a cross section through the turbine compartment 5, where the disruptive contour 9 is shown with a dotted line in the form of the protrusion 14 because it is situated in another plane.

Unlike what is shown in FIG. 2, the return air duct 8 here is arranged at the side next to an inlet air duct 21, so that the discharge port 12 can also extend over the total height of the turbine compartment 5. To improve the efficiency in a known way, the blades 11, which extend up to a rotor hub 35, may also be curved. Two neighboring blades 11 border the blade space 26 with the rotor hub 35.

FIG. 4 shows the turbine compartment without the rotor in a view of the wall 10 of the disruptive contour chamber 15, with the disruptive contour formed as a protrusion 14. The peripheral distance, related to the longitudinal axis 7, of the front edge of the protrusion 14 from the front edge 36 of the discharge port 12, as seen in the direction of flow, corresponds to an angle α of approximately 20° in the circumferential direction, wherein an arrangement anywhere on the entire circumference is possible, taking into account the distance from the front edge 36 of the discharge port 12. It has been found that particularly good results are achieved at an angle α of 30°, related to the discharge port 12.

A plurality of protrusions may also be provided to increase the braking effect, but it has been found that even one protrusion may be sufficient.

The radial length 1 of the protrusion 14, which extends radially inward from the outside circumference, takes up the total space available here and corresponds to 0.5 times the radius r of the rotor 6, which is shown with a dotted line.

This border comes about due to the fact that the rotor, which is shown with a dotted line, has a bearing shaft (not shown), which is guided in the head part 2, so that the turbine compartment 5 is always bordered centrally. In addition, a collar 33, which borders the disruptive contour chamber 15 radially, is also provided.

FIG. 5 shows that the rotor 6 may be provided with a braking contour 25 on its front side 13, this braking contour 25 being arranged here on the blades 11 and ending at a distance from the disruptive contour 14 in the disruptive contour chamber 15, wherein the gap 18 is now related to the braking contour 25. The turbine compartment 5 here must have a greater height on the whole. The shape of the disruptive contour 9 can be optimized in terms of fluid mechanics, wherein the protrusion 14 in turn has a width b and a height h.

Figure 6:
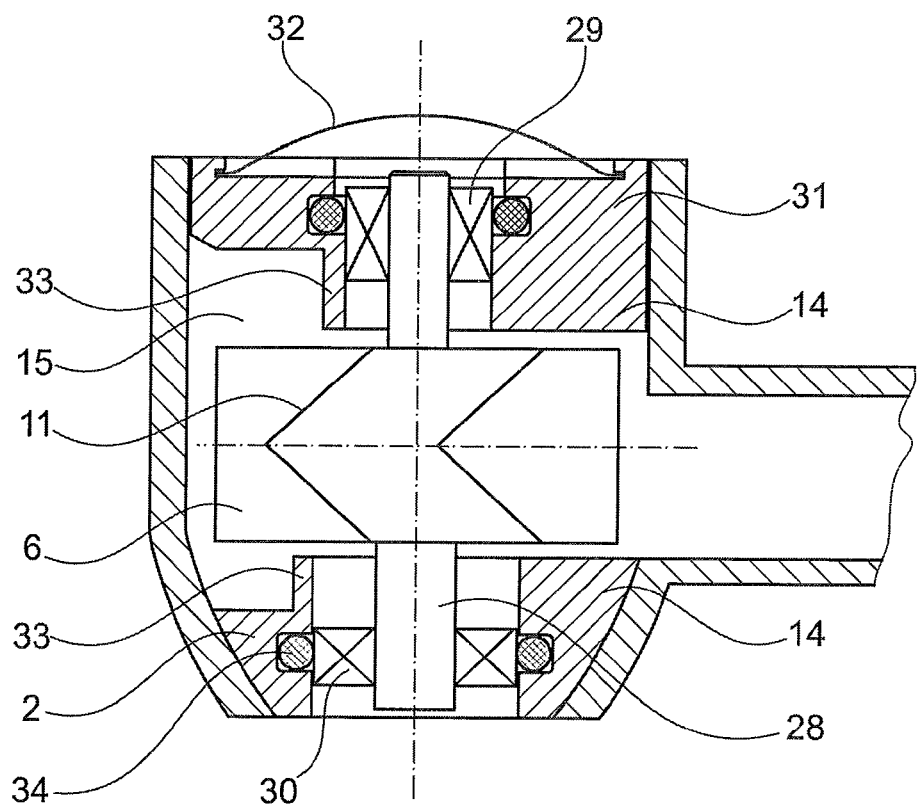
FIG. 6 an alternative embodiment having a disruptive contour chamber bordered by a collar.

As shown in FIG. 6, the disruptive contour chamber 15 is additionally bordered in the radial direction by a collar 33, which protrudes toward the rotor 6 and cooperates with the rotor 6, forming a gap with respect to a rotor shaft 28, which is supported by means of an upper bearing 29 and a lower bearing 30 directly or with the intermediate insertion of an intermediate part 31 with respect to the head part 2. The disruptive contour chamber 15 is therefore sealed with respect to the rotor shaft 28 and the bearings 29, 30 and the flow of the air stream used for braking toward the disruptive contour 9 in the form of the protrusion 14 may be guided efficiently. In the radial direction, the blades 11 of the rotor 6 end in a rotor hub 35, which is shown in FIG. 3, so that the collar 33, also shown in FIG. 4, is opposite the rotor hub 35 shown in FIG. 3.

The intermediate part 31 is screwed into the head part 2 and supports the upper bearing 29, which is supported elastically by means of an O-ring 34.

The invention claimed is:

1. A dental preparation instrument comprising:
   a turbine configured to drive a tool by compressed air;
   a rotor arranged in a turbine compartment and configured to rotate about its longitudinal axis,
      wherein the rotor includes blades extending up to a front side of the rotor,
      wherein the turbine compartment has a wall opposite the front side of the rotor and a discharge port for the compressed air communicating with a return air duct,
      wherein the discharge port is arranged so that at least parts of the blades pass by the discharge port in rotation about the longitudinal axis of the rotor,
      wherein the turbine compartment has a disruptive contour chamber adjacent to the front side of the rotor, and
      wherein a front side of the blades of the rotor facing the disruptive contour chamber is open toward the disruptive contour chamber; and
   a disruptive contour comprising at least one protrusion on the wall opposite the front side of the rotor, the at least one protrusion extends over a height in a direction of the longitudinal axis of the rotor.

2. The dental preparation instrument according to claim 1, wherein the disruptive contour is at a distance from the discharge port with an angle between 0° and 50°, inclusive, against a direction of rotation of the rotor.

3. The dental preparation instrument according to claim 1, wherein the height of the at least one protrusion is at least 0.25 mm in the direction of the longitudinal axis of the rotor, and
wherein a width of a gap between the disruptive contour and the front side of the rotor is no greater than 1 mm.

4. The dental preparation instrument according to claim 3, wherein a width of the disruptive contour, measured at an outside circumference of the blades, is at least 0.1 mm.

5. The dental preparation instrument according to claim 1, wherein the disruptive contour chamber is arranged above the rotor.

6. The dental preparation instrument according to claim 1, wherein the disruptive contour chamber is arranged beneath the rotor toward a side of the tool.

7. The dental preparation instrument according to claim 1, wherein the disruptive contour chamber is bordered on an inside radially by a collar cooperating with the rotor.

8. The dental preparation instrument according to claim 7, wherein the disruptive contour is arranged on an outside circumference of a wall of a braking chamber and extends radially at least partially up to the collar.

9. The dental preparation instrument according to claim 1, wherein a braking contour, which cooperates with the disruptive contour, is provided on a front side of the blades of the rotor facing the disruptive contour chamber.

10. The dental preparation instrument according to claim 1, wherein the disruptive contour chamber is bordered by a cover module comprising at least one cover and one intermediate part supporting the at least one cover that is connected to the housing.

11. A dental apparatus, comprising:
a turbine constructed to drive a tool by compressed air, the turbine includes:
a rotor constructed to rotate about its longitudinal axis, and
a plurality of blades that extend up to a front side of the rotor; and
a turbine compartment that includes:
a disruptive contour in the form of a protrusion extending from a wall of the turbine compartment, and
a discharge port communicatively connected to a return air duct,
wherein the discharge port is arranged such that parts of the plurality of blades pass by the discharge port during a rotation of the rotor about the longitudinal axis of the rotor.

12. The dental apparatus according to claim 11, wherein an angle between (i) a radial line emanating from the longitudinal axis of the rotor and intersecting a portion of the disruptive contour and (ii) another radial line emanating from the longitudinal axis of the rotor and intersecting with a portion of the discharge port is between 10°-50°.

13. The dental apparatus according to claim 12, wherein the angle is 30°.

14. The dental apparatus according to claim 11,
wherein a distal portion of the disruptive contour is at least 0.25 mm from the wall of the turbine compartment, and
wherein a gap between the distal portion of the disruptive contour and the front side of the rotor is no greater than 1 mm.

15. The dental apparatus according to claim 14, wherein a width of the distal portion of the disruptive contour in a direction perpendicular to a radial line emanating from the longitudinal axis of the rotor is no less than 0.1 mm.

16. The dental apparatus according to claim 11, wherein a portion of the turbine compartment is a disruptive contour chamber, and the disruptive contour chamber is located above the rotor.

17. The dental apparatus according to claim 11, wherein a portion of the turbine compartment is a disruptive contour chamber, and the disruptive contour chamber is located beneath the rotor.

18. The dental apparatus according to claim 11, wherein a portion of the turbine compartment is a disruptive contour chamber, and
wherein the disruptive contour chamber is bordered on an inside radially by a collar that cooperates with the rotor.

19. The dental apparatus according to claim 18, wherein the disruptive contour extends up to the collar in a direction of the longitudinal axis of the rotor.

20. The dental apparatus according to claim 11, wherein a braking contour is provided on a side of each of the plurality of blades.

21. The dental apparatus according to claim 11, wherein a portion of the turbine compartment is a disruptive contour chamber, and
wherein the disruptive contour chamber is bordered by a cover module that comprises a cover and an intermediate part that supports the cover.

22. The dental apparatus according to claim 11,
wherein a portion of the turbine compartment is a disruptive contour chamber, and the disruptive contour chamber is located to a side of the rotor.

* * * * *